United States Patent [19]

Dhabhar et al.

[11] 4,283,385

[45] Aug. 11, 1981

[54] DENTIFRICES WITH IMPROVED SOLUBLE FLUORIDE AVAILABILITY

[75] Inventors: Dadi J. Dhabhar, Norwalk, Conn.; Nutan B. Shah, New Rochelle, N.Y.

[73] Assignee: Richardson-Merrell Inc., Wilton, Conn.

[21] Appl. No.: 148,548

[22] Filed: May 9, 1980

[51] Int. Cl.[3] .......... A61K 7/18

[52] U.S. Cl. .......... 424/52; 424/57; 424/54

[58] Field of Search .......... 424/52, 54, 57

[56] References Cited

U.S. PATENT DOCUMENTS

| | | | |
|---|---|---|---|
| 2,975,102 | 3/1961 | Matsumura et al. | 424/49 |
| 3,004,897 | 10/1961 | Shore | 424/54 |
| 3,558,769 | 1/1971 | Globus | 424/54 |
| 3,699,221 | 10/1972 | Schole et al. | 424/54 |
| 3,988,434 | 10/1976 | Schole et al. | 424/54 |
| 4,051,234 | 9/1977 | Gieske | 424/52 |
| 4,080,440 | 3/1978 | DiGuilio et al. | 424/52 X |
| 4,083,955 | 4/1978 | Grabon Stetter | 424/52 X |
| 4,137,303 | 1/1979 | Gaffar et al. | 424/52 |
| 4,177,258 | 12/1979 | Gaffar et al. | 424/52 |
| 4,183,915 | 1/1980 | Gaffar et al. | 424/52 |

FOREIGN PATENT DOCUMENTS 490384 2/1937 United Kingdom .

*Primary Examiner*—Shep K. Rose

*Attorney, Agent, or Firm*—George W. Rauchfuss, Jr.

[57] ABSTRACT

Dentifrice preparations having improved soluble fluoride availability are obtained by incorporation of ethylenediamine tetraacetic acid and sodium salts thereof.

8 Claims, No Drawings

DENTIFRICES WITH IMPROVED SOLUBLE FLUORIDE AVAILABILITY

FIELD OF THE INVENTION

This invention relates to dentifrices containing fluoride and is particularly concerned with toothpastes containing calcium carbonate or various calcium phosphates as the abrasive.

BACKGROUND OF THE INVENTION

It has long been known that a treatment of tooth surfaces with fluorides, such as sodium monofluorophosphate, has a caries inhibiting effect. To obtain this effect, fluoride compounds have been incorporated into toothpastes. However, a dentifrice containing a soluble fluoride and calcium carbonate or calcium phosphates looses an appreciable amount of fluorine in the composition upon aging. It has been found that the calcium containing compounds remove the soluble fluoride from the composition by forming insoluble and inactive calcium fluoride thereby inhibiting the anticariogenic effect of the fluoride.

It is, therefore, an object of this invention to provide dentifrice compositions containing fluorides and calcium containing abrasives having improved levels of soluble fluoride availability.

SUMMARY OF THE INVENTION

It has now been surprisingly found that the inactivation of soluble fluoride by various calcium containing abrasives in dentifrices may be inhibited by the incorporation of minor amounts of ethylenediamine tetraacetic acid or sodium salt thereof in the dentifrice composition.

DETAILED DESCRIPTION OF THE INVENTION

It has been discovered that the addition of a minor amount of ethylenediamine tetraacetic acid or sodium salt thereof to a fluoride containing dentifrice having a calcium abrasive system will improve the level of soluble fluoride availability and reduce the formation of insoluble fluoride. The minor amount of inhibitor compound employed in the dentifrice compositions will generally be from about 0.01 to about 5.0% by weight based on the total weight of the composition, preferably from about 0.05 to about 1% and most preferably from about 0.1 to about 0.5% by weight. In addition to ethylenediamine tetraacetic acid, there may be employed mono-, di- tri- and tetra- sodium salts thereof as well as penta sodium diethylenetriaminepentaacetate. Preferred for use in this invention is the tetrasodium salt of ethylenediamine tetraacetic acid available from GAF Corporation, New York, N.Y. as under the trademark CHEELOX BF-78 sequestrant.

Among the calcium compounds utilized as abrasive in the dentifrices of this invention there may be employed calcium carbonate and various calcium phosphates such as dicalcium phosphate, tricalcium phosphate, calcium pyrophosphate and the like. The total content of abrasive agent in the dentifrice is variable but will generally be up to about 90% by weight of the total composition. Generally, however, the abrasive will be present in an amount of from about 5 to about 60% by weight, preferably from about 20 to about 50% by weight and most preferably from about 25 to about 45% by weight. Especially preferred as the calcium abrasive is calcium carbonate.

The preferred fluoride component of the dentifrice composition is sodium monofluorophosphate although other monofluorophosphate salts and other water-soluble fluorides may also be employed. In addition to sodium monofluorophosphate, $Na_2PO_3F$, other monofluorophosphate salts which have sufficient water solubility for use in the instant invention include calcium monofluorophosphate, magnesium monofluorophosphate and aluminum monofluorophosphate. In accordance with this invention the term "monofluorophosphate" also includes monofluoropolyphosphates such as $Na_4P_3O_9F$, $K_4P_3O_9F$, $(NH_4)_4P_3O_9F$, $Na_3KP_3O_9F$, $(NH_4)_3NaP_3O_9F$ and $Li_4P_3O_9F$. Other suitable water soluble fluorides useful in the compositions of this invention include, for example, stannous fluoride, sodium fluoride, potassium fluoride, lithium fluoride, ammonium fluoride, cupric fluoride, and the like. The fluorides will generally be present in the dentifrice compositions in an amount of from about 0.1 to about 5.0 weight percent based on the total weight of the composition and preferably in an amount of from about 0.5 to about 1% and most preferably in an amount of from about 0.75 to about 0.85% by weight.

Any suitable surface active or detersive material may be included in the dentifrice compositions. Such compatible materials are desirable to provide additional detersive, foaming and anti-bacterial properties depending upon the specific type of surface active material. These detergents are usually water-soluble organic compounds and may be anionic, nonionic or cationic in structure. It is usually preferred to use the water-soluble non-soap or synthetic organic detergents. Suitable detersive materials are known and include, for example, the water-soluble salts of higher fatty acid monoglyceride monosulfate detergents (e.g. sodium coconut fatty acid monoglyceride monosulfate), higher alkyl sulfate (e.g. sodium lauryl sulfate), alkyl aryl sulfonate (e.g. sodium dodecyl benzene sulfonate), higher fatty acid esters of 1,2-dihydroxy propane sulfonate (e.g. sodium coconut fatty acid ester of 1,2-dihydroxy propane sulfonate), and the like. The various surface active materials may be used in any suitable amount, generally from about 0.05 to about 10 percent by weight, and preferably from about 0.5 to 5 percent by weight of the dentifrice composition.

In dental cream formulations, the liquids and solids should be proportioned to form an extrudable creamy mass of desirable consistency. In general, liquids in the dental cream will comprise chiefly water, glycerin, sorbitol, propylene glycol, or the like, including suitable mixtures thereof. It is advantageous usually to use a mixture of both water and a humectant or binder such as glycerin or sorbitol. It is preferred to use glycerin. The total liquid content will generally be about 20 to 75 percent by weight of the formulation. It is also preferred to use a gelling agent in dental creams such as the natural and synthetic gum and gum-like material, e.g. Irish moss, gum tragacanth, sodium carboxymethylcellulose, polyvinylpyrrolidone, starch, and the like. The Irish moss and sodium carboxymethylcellulose are compatible particularly and are preferred gelling agents. The gum content is usually in an amount up to about 10 percent and preferably about 0.5 to 5 percent by weight of the formulation.

Various other materials may be incorporated in the oral preparations of this invention. Examples thereof are coloring or whitening agents, preservatives, silicones, chlorophyll compounds, ammoniated materials such as urea, diammonium-phosphate and mixtures thereof, and other constituents. These adjuvants are incorporated in the instant compositions in amounts which do not substantially adversely affect the properties and characteristics suitably selected and used in proper amount depending upon the particular type of preparation involved.

For some purposes it may be desirable to include antibacterial agents in the compositions of the present invention. Typical antibacterial agents which may be used in amounts of about 0.01 percent to about 5 percent, preferably about 0.05 percent to about 1.0 percent, by weight of the dentifrice composition include: $N^1$-4(chlorobenzyl)-$N^5$-2,4-dichlorobenzyl)biguanide, p-chlorophenyl biguanide, 4-chlorobenzhydryl biguanide, 4-chlorobenzhydrylguanylurea, N-3-lauroxpropyl-$N^5$-p-chlorobenzylbiguanide, 1,6-di-p-chlorophenylbiguanidohexane, 1-lauryldimethylammonium)-8-(p-chlorobenzyldimethylammonium) octane dichloride, 5,6-dichloro-2-guanidinobenzimidazole, $N^1$-p-chlorphenyl-$N^5$-laurylbiguanide, 5-amino-1,3-bis(2-ethylexyl)-5-methylhexahydropyrimidine, and their non-toxic acid addition salts.

Tooth desensitization agents such as, for example, a nitrate of potassium, lithium or sodium disclosed in U.S. Pat. No. 3,863,006 issued Jan. 28, 1975, to Milton Hodosh, may also be incorporated in the dentifrice compositions in tooth desensitizing amounts, generally up to about 20% and preferably about 5% by weight.

Any suitable flavoring or sweetening materials may be employed in formulating a flavor for the compositions of the present invention. Examples of suitable flavoring constituents include the flavoring oils, e.g. oils of spearmint, peppermint, wintergreen, sassafras, clove, sage, eucalyptus, marjoram, cinnamon, lemon and orange, as well as sodium methylsalicylate. Suitable sweetening agents include sucrose, lactose, maltose, sorbitol, sodium cyclamate, ammonium glycyrrhizinate and its derivatives and saccharin. Suitably, flavor and sweetening agent may together comprise from about 0.01 to 5 percent or more of the compositions of the instant invention.

The dental cream should have a pH practicable for use. A neutral to basic pH is particularly desirable. The initial pH range of about 7 to 9.5 preferably 7.5, is considered the most practicable for use. Where reference is made to pH herein, it is intended that such pH determination be made on the dental cream directly. If necessary, basic materials may be added to adjust the pH as desired.

The ethylenediamine tetraacetic acid or sodium salts thereof are to be added to the formulation containing the calcium abrasive prior to the incorporation of the fluoride in order to tie up the free calcium ions prior to the incorporation of the fluoride.

Dentifrice compositions of this invention containing the ethylenediamine tetraacetic acid or a sodium salt thereof maintain substantially higher levels of soluble fluoride than similar compositions without the named ingredient.

The following specific examples are further illustrative of the nature of the present invention, but it is to be understood that the invention is not limited thereto. The compositions are prepared in the usual manner and all amounts of the various ingredients are by weight unless otherwise specified.

EXAMPLES

The following dental creams of this invention were prepared:

| Ingredient | A %w/w | B %w/w | C %w/w |
|---|---|---|---|
| Calcium Carbonate | 35.0 | 30.0 | 35.0 |
| Glycerin | 12.5 | 12.25 | 12.5 |
| Sorbitol Solution 70° | 12.5 | 9.0 | 12.5 |
| Potassium Nitrate | — | 5.0 | — |
| Colloidal Silica | 1.7 | 1.0 | 1.7 |
| Sodium Monofluorophosphate | 0.82 | 0.81 | 0.82 |
| Veegum Regular | 0.8 | — | 0.8 |
| Xanthan Gum | — | 0.38 | — |
| Sodium Carboxymethylcellulose | 0.7 | 0.92 | 0.7 |
| Tetrasodium salt of Ethylenediamine Tetraacetic Acid | 0.3 | 0.3 | 0.1 |
| Sodium Saccharin | 0.2 | 0.23 | 0.2 |
| Flavoring | 1.4 | 1.35 | 1.4 |
| Alcohol USP 190° | 0.5 | — | 0.5 |
| Sodium Lauryl Sulfate | 1.5 | 2.1 | 1.5 |
| Methylparaben | 0.06 | 0.06 | 0.06 |
| Propylparaben | 0.02 | 0.02 | 0.02 |
| Water | 32.0 | 36.58 | 32.2 |

Composition C as well as a control composition identical to Composition C except that the tetrasodium salt of ethylenediamine tetraacetic acid is omitted from the formulation were aged at 45° and at 25° with the amount of total soluble fluoride determined in ppm periodically. The results are as indicated in the table below:

| | Total Soluble Fluoride (ppm) Months/Temperature | | | |
|---|---|---|---|---|
| Composition | Initial | 1 mo/45° | 3 mo/25° | 6 mo/25° |
| A | 1010 | 660 | 830 | 700 |
| Control | 1130 | 370 | 680 | 450 |

It is evident that the composition of this invention retains soluble fluoride better than similar compositions without the ethylenediamine tetraacetic acid compound.

It will be apparent to one skilled in the art that modifications of the above examples may be made thereto by those skilled in the art.

We claim:

1. A dentifrice comprising from about 0.1 to about 5% by weight of a water-soluble fluoride, from about 5 to about 60% by weight of a calcium abrasive and from about 0.01 to about 5% by weight of ethylenediamine tetraacetic acid or sodium salt thereof.

2. The dentifrice of claim 1 wherein the water soluble fluoride is a monofluorophosphate salt and the abrasive is selected from calcium carbonate or a calcium phosphate.

3. The dentifrice of claim 2 wherein the water-soluble fluoride is sodium monofluorophosphate, the abrasive is calcium carbonate and the ethylenediamine tetraacetic acid salt is the tetrasodium salt of ethylenediamine tetraacetic acid.

4. The dentifrice of claim 3 comprising from about 0.05 to about 1% by weight tetrasodium salt of ethylenediamine tetraacetic acid, from about 20 to about 50% by weight calcium carbonate and from about 0.5 to about 1% by weight sodium monofluorophosphate.

5. The dentifrice of claim 4 comprising from about 0.1 to about 0.5% by weight tetrasodium salt of ethylenediamine tetraacetic acid, from about 25 to about 45% by weight calcium carbonate and from about 0.75 to about 0.85% by weight sodium monofluorophosphate.

6. The dentifrice of claim 4 comprising a dental cream having the formula:

| Ingredient | Composition A %w/w |
|---|---|
| Calcium Carbonate | 35.0 |
| Glycerin | 12.5 |
| Sorbitol Solution 70% | 12.5 |
| Colloidal Silica | 1.7 |
| Sodium Monofluorophosphate | 0.82 |
| Veegum Regular | 0.8 |
| Sodium Carboxymethylcellulose | 0.7 |
| Tetrasodium salt of Ethylenediamine Tetraacetic Acid | 0.3 |
| Sodium Saccharin | 0.2 |
| Flavoring | 1.4 |
| Alcohol USP 190° | 0.5 |
| Sodium Lauryl Sulfate | 1.5 |
| Methylparaben | 0.06 |
| Propylparaben | 0.02 |
| Water | 32.0 |

7. The dentifrice of claim 4 comprising a dental cream having the formula:

| Ingredient | Composition B %w/w |
|---|---|
| Calcium Carbonate | 30.0 |
| Glycerin | 12.25 |
| Sorbitol Solution 70% | 9.0 |
| Potassium Nitrate | 5.0 |
| Colloidal Silica | 1.0 |
| Sodium Monofluorophosphate | 0.81 |
| Xanthan Gum | 0.38 |
| Sodium Carboxymethylcellulose | 0.92 |
| Tetrasodium salt of Ethylenediamine Tetraacetic Acid | 0.3 |
| Sodium Saccharin | 0.23 |
| Flavoring | 1.35 |
| Sodium Lauryl Sulfate | 2.1 |
| Methylparaben | 0.06 |
| Propylparaben | 0.02 |
| Water | 36.58 |

8. The dentifrice of claim 4 comprising a dental cream having the formula:

| Ingredient | Composition C %w/w |
|---|---|
| Calcium Carbonate | 35.0 |
| Glycerin | 12.5 |
| Sorbitol Solution 70% | 12.5 |
| Colloidal Silica | 1.7 |
| Sodium Monofluorophosphate | 0.82 |
| Veegum Regular | 0.8 |
| Sodium Carboxymethylcellulose | 0.7 |
| Tetrasodium salt of Ethylenediamine Tetraacetic Acid | 0.1 |
| Sodium Saccharin | 0.2 |
| Flavoring | 1.4 |
| Alcohol USP 190° | 0.5 |
| Sodium Lauryl Sulfate | 1.5 |
| Methylparaben | 0.06 |
| Propylparaben | 0.02 |
| Water | 32.2 |

* * * * *